US00PP32054P2

(12) United States Plant Patent
Dirr

(10) Patent No.: US PP32,054 P2
(45) Date of Patent: Aug. 11, 2020

(54) ***HYDRANGEA* PLANT NAMED 'COF-HM1'**

(50) Latin Name: *Hydrangea macrophylla*
Varietal Denomination: COF-HM1

(71) Applicant: Michael Dirr, Bogart, GA (US)

(72) Inventor: Michael Dirr, Bogart, GA (US)

( * ) Notice: Subject to any disclaimer, the term of this patent is extended or adjusted under 35 U.S.C. 154(b) by 0 days.

(21) Appl. No.: 16/501,958

(22) Filed: Jul. 9, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — Cassandra Bright

(57) ABSTRACT

A new and distinct *Hydrangea* cultivar named 'COF-HM1' is disclosed, characterized by compact plants producing mop-head inflorescences with pink or blue flowers, depending upon the absence or presence of aluminum. Plants are well-suited to commercial applications, having a rapid production cycle. Rebloom potential is increased in plants of the new variety, which rebloom on both new growth and old wood. Plants of the new variety are cold hardy and bloom abundantly. The new variety is a *Hydrangea*, normally produced as an ornamental plant.

4 Drawing Sheets

Latin name of the genus and species: *Hydrangea macrophylla.*

Variety denomination: 'COF-HM1'.

BACKGROUND OF THE INVENTION

The new *Hydrangea* cultivar was found and selected as an isolated specimen in a garden setting in Bishop, Ga., during May of 2015. The seed and pollen parents are unknown.

Asexual reproduction of the new cultivar 'COF-HM1' by vegetative soft wood cuttings was first performed during July of 2015, at a commercial greenhouse in Watkinsville, Ga. Subsequent propagation has shown that the unique features of this cultivar are stable and reproduced true to type in 5 successive generations.

SUMMARY OF THE INVENTION

The cultivar 'COF-HM1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COF-HM1' These characteristics in combination distinguish 'COF-HM1' as a new and distinct *Hydrangea* cultivar:

1. Extremely floriferous.
2. Increased rebloom potential, reblooming on both new growth and old wood (previous season's growth).
3. Observed more cold hardy than other remontant *Hydrangea.*
4. Compact habit of approximately 5 to 6 feet high and 5 to 6 feet wide at maturity.
5. Pink or blue mophead depending on absence/presence of aluminum, respectively. Easy and fast response to blue treatment, turning blue with one application of aluminum sulfate.
6. Rapid production cycle.

COMMERCIAL COMPARISON

Plants of the new cultivar 'COF-HM1' can be compared to the variety *Hydrangea macrophylla* 'Bailmer', U.S. Plant Pat. No. 15,298. These varieties are similar in most horticultural characteristics; however 'COF-HM1' differs in the following:

1. The new variety reblooms faster than this comparator.
2. The new variety has a faster production cycle than this comparator.
3. The new variety is more cold hardy than this comparator.
4. The new variety produces more flowers than this comparator.

Plants of the new cultivar 'COF-HM1' can be compared to the variety *Hydrangea macrophylla* 'Monmar', U.S. Plant Pat. No. 25,209. These varieties are similar in most horticultural characteristics; however 'COF-HM1' differs in the following:

1. The new variety reblooms faster than this comparator.
2. The new variety has a faster production cycle than this comparator.
3. The new variety produces deeper blue flowers than this comparator. When not treated with aluminum the new variety produces much deeper pink flowers than this comparator.
4. The new variety produces more flowers than this comparator.

BRIEF DESCRIPTION OF THE PHOTOGRAPHS

The accompanying photograph in FIG. 1 illustrates in full color a typical inflorescence of 'COF-HM1' having no aluminum treatment.

Figure 1:
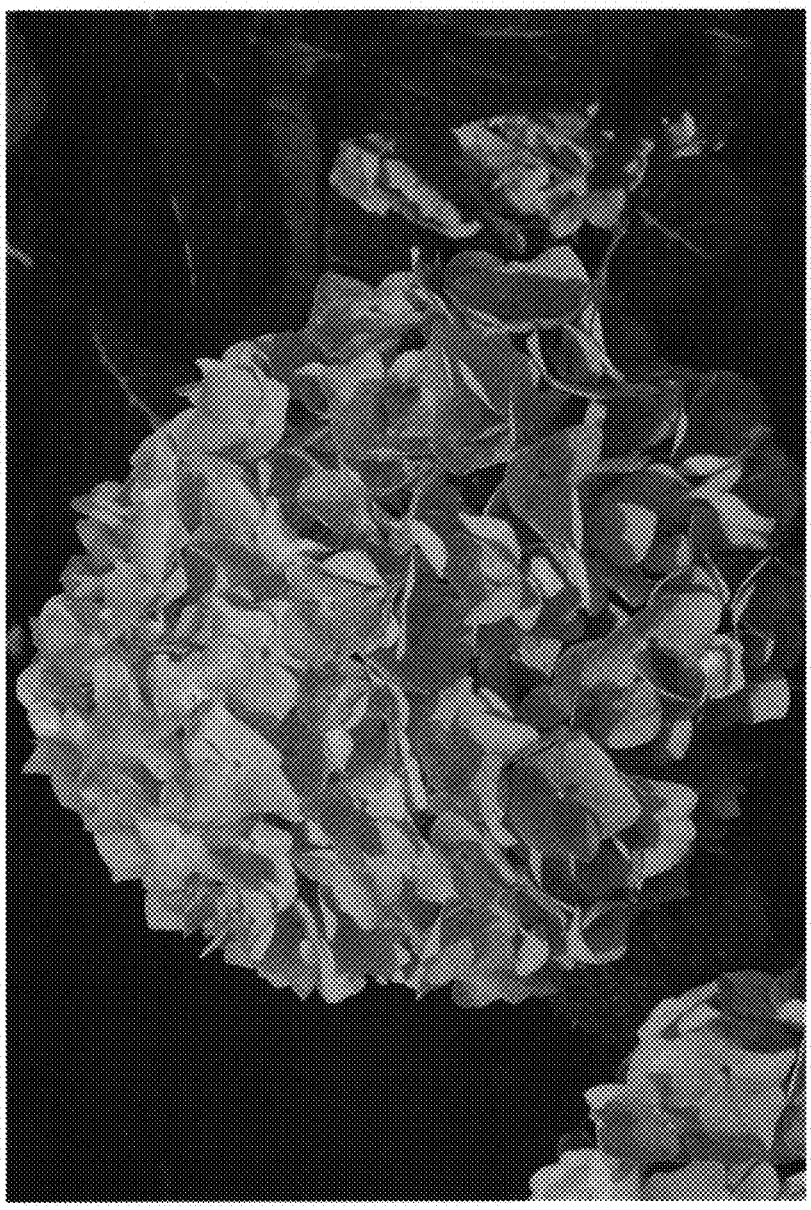
Figure 2:
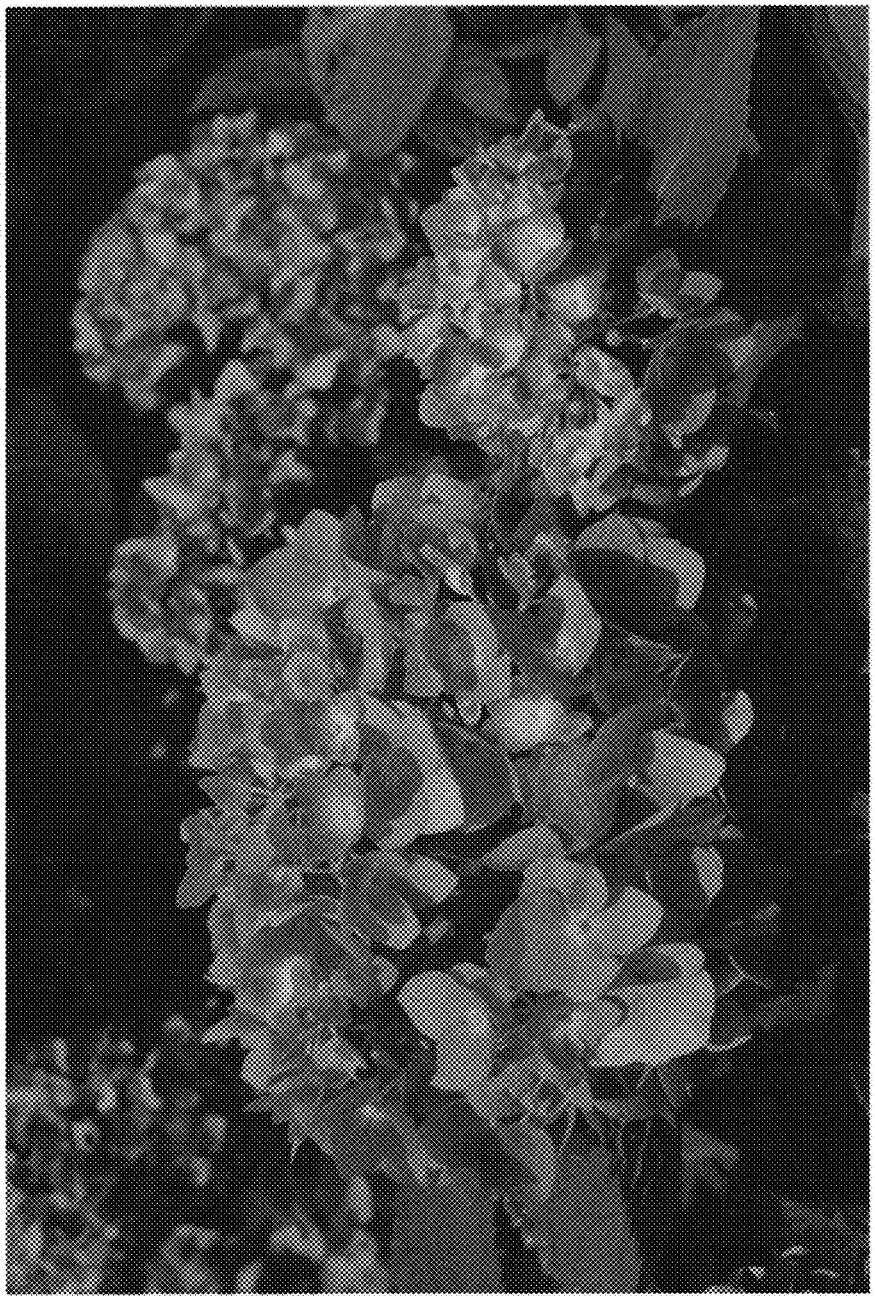
FIG. 2 illustrates a typical inflorescence of 'COF-HM1' given a typical aluminum sulfate treatment of 70 grams top dressed.
Figure 3:
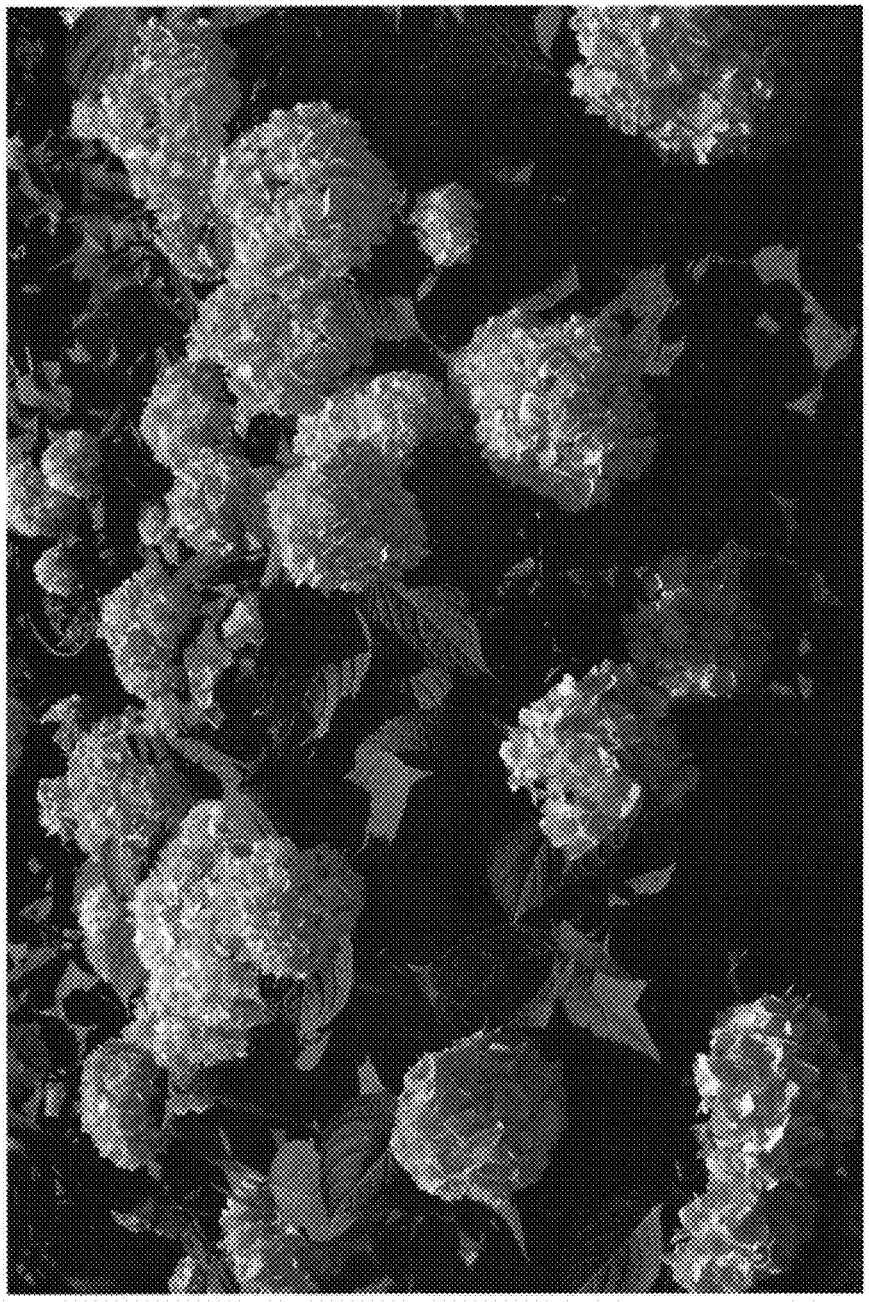
FIG. 3 illustrates in full color a typical plant of 'COF-HM1' in a 10 gallon pot, untreated with aluminum. Plant in the photographs is approximately 18 months old, in a 10-gallon pot.
Figure 4:
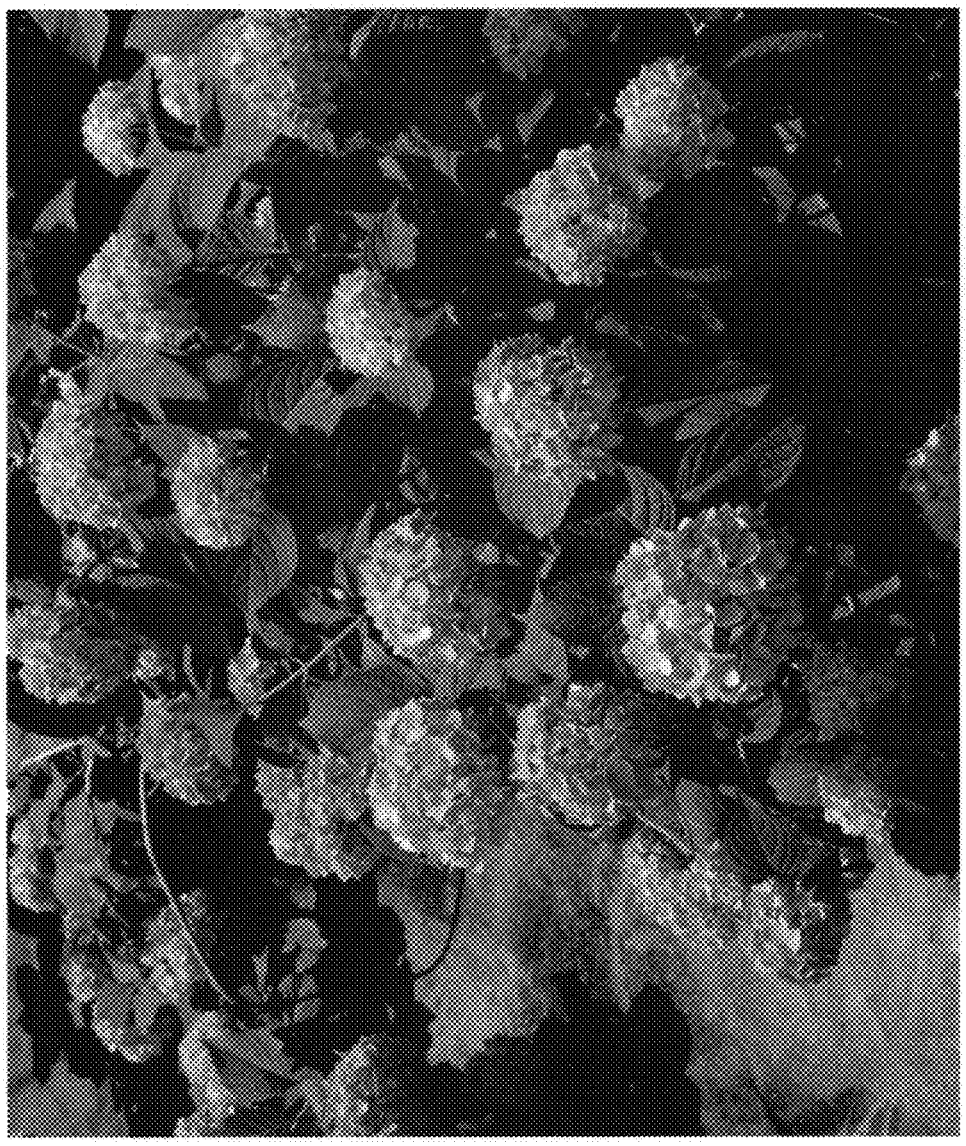
FIG. 4 illustrates another typical plant of 'COF-HM1' in a 10 gallon pot, this plant treated with aluminum.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'COF-HM1' plants grown in a commercial greenhouse in Watkinsville, Ga., outdoors under 50% saran shade. Measurements were taken during May of 2019. The plants were about 18 months old planted in 10-gallon pots. The growing temperature ranged from 15° C. to 25° C. during the day, and 10° C. to 15° C. at night. Measurements and numerical values represent averages of typical plant types.

Botanical classification: *Hydrangea macrophylla* 'COF-HM1'.

PROPAGATION

Time to rooting: 21 to 28 days at approximately 20° to 25° C.

Time to produce a flowering plant: 1 year to produce a full, flowering plant from a rooted cutting.

PLANT

Growth habit: Densely branched.
Overall plant shape: Broad, rounded.
Height: Approximately 60 cm.
Plant spread: Approximately 75 cm.
Growth rate: Slow to moderate.
Branching characteristics:
Length of lateral branches/stems: Approximately 40 cm.
Number of lateral branches: Approximately 20.
Diameter of lateral branches: Approximately 0.5 to 0.75 cm.
Pinching required: Yes. Prune 2 to 3 times in production cycle.
Lateral branch shape: Round.
Lateral branch strength: Strong.
Lateral branch/stem color: Near RHS Green 140B.
Branch angle: 20° to 30°.
Other stem or plant characteristics:
- *Lenticel length*.—Approximately 2.5 mm.
- *Lenticel width*.—Approximately 0.5 mm.
- *Lenticel color*.—Near RHS Grey-Brown 199A.

Number of leaves per lateral branch: Average 12.
Root description: Profuse, diffuse, well branched, RHS White 155D.
Age of plant described: Approximately 18 months from a rooted cutting.

FOLIAGE

Leaf:
- *Arrangement*.—Opposite.
- *Compound or single*.—Single (simple leaf).
- *Average length*.—Approximately 15 cm.
- *Average width*.—Approximately 8 cm.
- *Shape of blade*.—Ovate.
- *Lobing*.—None.
- *Apex*.—Short acuminate.
- *Base*.—Cuneate.
- *Attachment*.—With petiole.
- *Margin*.—Serrate.
- *Texture of top surface*.—Rough, veins deeply impressed.
- *Texture of bottom surface*.—Rough.
- *Leaf internode length*.—Approximately 6 cm.
- *Color*.—Young foliage upper side: Near RHS Green 136A. Young foliage under side: Near RHS Green 137B. Mature foliage upper side: Near RHS Green 133A. Mature foliage under side: Near RHS Green 138A.
- *Venation*.—Type: Pinnate with deeply impressed veins. Venation color upper side: Near RHS Yellow-Green 147C. Venation color under side: Near RHS Yellow-Green 147B.
- *Durability of foliage to stresses*.—Moderate.

Petiole:
- *Average length*.—Approximately 3 cm.
- *Diameter*.—Approximately 3 mm.
- *Texture*.—Glabrous.
- *Color*.—Near RHS Yellow-Green 145B.

FLOWER

Bloom period:
- *Natural season*.—May-June. Thereafter flowering on new growth of the season into October in Athens, Ga.
- *Flowering continuous, sporadic, intermittent, or other*.—Continuous, remontant.

Inflorescence:
- *Type*.—Corymb.
- *Shape*.—Rounded-globose.
- *Height*.—Approximately 10 cm.
- *Width*.—Approximately 15 cm.
- *Quantity of flowers per inflorescence*.—Fertile flowers: Approximately 45. Sterile Flowers: Approximately 160.

Bud:
- *Bud shape*.—Round.
- *Bud length*.—Approximately 2 mm.
- *Bud diameter*.—Approximately 2 mm.
- *Bud color*.—Near RHS Yellow-Green 144C.
- *Base/calyx*.—Near RHS Yellow-Green 144C.

Sterile flowers: Petals not observed to open.
Sterile flower sepal:
- *Arrangement*.—Clustered on a pedicel.
- *Number*.—3 to 5 per cluster.
- *Shape*.—Broad ovate to rounded.
- *Tip*.—Abrupt. Essentially rounded.
- *Base*.—Rounded.
- *Margin*.—Entire.

*Length.*—1.5 cm.
*Width.*—1.5 cm.
*Texture, upper.*—Fine.
*Texture, lower.*—Fine.
*Color.*—Upper surface at first opening: Acidic: Near RHS Blue 101B. Basic: Near RHS Purple 75A. Upper surface at maturity: Acidic: Near RHS Blue 101B. Basic: Near RHS Red-Purple 73B. Under surface at first opening: Acidic: Near RHS Blue 100C. Basic: Near RHS Purple 75C. Under surface at maturity: Acidic: Near RHS Blue 100D. Basic: Near RHS Purple 75D. Fading to Upper surface: Acidic: Near RHS Blue 100B. Basic: Near RHS Red-Purple 69A. Fading to Under surface: Acidic: Near RHS Blue 100D. Basic: Near RHS Red-Purple 69D.

Sterile flower pedicel:
*Length.*—1.3 cm.
*Diameter.*—1 mm.
*Angle.*—30°.
*Strength.*—Flimsy.
*Texture.*—Fine.
*Color.*—Acidic: Near RHS Violet-Blue 91B. Basic: Near RHS Red-Purple 68D.

Fertile flower:
*Bud shape.*—Round.
*Bud length.*—2 mm.
*Bud diameter.*—3 mm.
*Bud color.*—Acidic: Near RHS Blue 100C. Basic: Near RHS Green 135D.
*Flower aspect.*—Not showy.
*Flower shape.*—Star-shaped.
*Flower length.*—3 mm.
*Flower diameter.*—5 mm.
*Flower depth.*—2 mm.
*Self-cleaning/persistent.*—Appear to be self-cleaning.

Fertile flower petals:
*Length of petal.*—2 mm.
*Width of petal.*—1.5 mm.
*Apex.*—Rounded.
*Shape of petal.*—Obovate.
*Petal margin.*—Entire.
*Petal arrangement.*—Five petals, actinomorphic.
*Petal number.*—5.
*Petal base.*—Cuneate.
*Petals fused.*—Free.
*Petal texture.*—Fine.
*Color.*—Upper surface at first opening: Acidic: Near RHS Green 142B. Basic: Near RHS Green 142B. Upper surface at maturity: Acidic: Near RHS Blue 100B. Basic: Near RHS Red-Purple 73B. Under surface at first opening: Acidic: Near RHS Green 142C. Basic: Near RHS Green 142C. Under surface at maturity: Acidic: Near RHS Blue 100C. Basic: Near RHS Red-Purple 73C. Upper surface fading to: Acidic: Near RHS Blue 100D. Basic: Near RHS Red-Purple 73D. Lower surface fading to: Acidic: Near RHS Blue 100D. Basic: Near RHS Red-Purple 73D.

Fertile flower sepal:
*Arrangement.*—Solitary.
*Number.*—5.
*Shape.*—Star-shaped.
*Tip.*—Acute.
*Base.*—Truncate.
*Margin.*—Entire.
*Length.*—1 mm.
*Width.*—1 mm.
*Texture, upper.*—Fine.
*Texture, lower.*—Fine.
*Color.*—Upper surface at first opening: Near RHS Blue 101C. Upper surface at maturity: Near RHS Blue 101C. Under surface at first opening: Near RHS Blue 101D. Under surface at maturity: Near RHS Blue 101C. Upper surface fading to: Near RHS Blue 101C. Lower surface fading to: Near RHS Blue 101C.

Fertile flower pedicel:
*Angle.*—40°.
*Strength.*—Moderate.
*Length.*—3 mm.
*Width.*—Less than 1 mm.
*Texture.*—Fine.
*Color, same basic or acidic.*—Near RHS Violet-Blue 98B.

Peduncle:
*Length.*—Approximately 4 cm.
*Diameter.*—Approximately 3 mm.
*Texture.*—Medium.
*Angle.*—70°.
*Strength.*—Strong.
*Color.*—Near RHS Blue 100C.

REPRODUCTIVE ORGANS

Sterile flower: Not observed.

Fertile flower:
*Stamen number.*—10.
*Filament length.*—3 mm.
*Filament color.*—Near RHS Blue 101C.
*Anther shape.*—Oblong.
*Anther length.*—1 mm.
*Anther color.*—Near RHS Blue 101C.
*Pollen amount.*—Present but minimal.
*Pollen color.*—Near RHS White 155B.

Gynoecium:
*Pistil number.*—1.
*Pistil length.*—2 mm.
*Stigma shape.*—Flattened.
*Stigma color.*—Near RHS Blue 101C.
*Style length.*—Less than 1 mm.
*Style color.*—Near RHS Blue 101C.
*Ovary color.*—Near RHS Blue 101C.

OTHER CHARACTERISTICS

Fruit/seed production: Not observed.

Disease resistance: No more or less than other *H. macrophylla* although high resistance to mildew. Susceptible to *Cercospora* in wet years.

Drought tolerance and cold tolerance/temperature range: Similar to most *H. macrophylla*, zone 6 to 8 adaptability with the caveat that flowers form on new growth.

What is claimed is:

1. A new and distinct cultivar of *Hydrangea* plant named 'COF-HM1' as herein illustrated and described.

* * * * *